US009693564B2

United States Patent
Reubens

(10) Patent No.: US 9,693,564 B2
(45) Date of Patent: Jul. 4, 2017

(54) WATER BASED ANTIMICROBIAL COMPOSITION USING BENZALKONIUM CHLORIDE AND COCAMIDOPROPYL PG-DIMONIUM CHLORIDE PHOSPHATE

(71) Applicant: SAFEHANDS SOLUTIONS, LLC, Oxford, MA (US)

(72) Inventor: Jay Reubens, Boca Raton, FL (US)

(73) Assignee: SAFEHANDS SOLUTIONS, LLC, Oxford, MA (US)

(*) Notice: Subject to any disclaimer, the term of this patent is extended or adjusted under 35 U.S.C. 154(b) by 0 days.

(21) Appl. No.: 14/968,959

(22) Filed: Dec. 15, 2015

(65) Prior Publication Data

US 2016/0095318 A1   Apr. 7, 2016

Related U.S. Application Data

(63) Continuation-in-part of application No. 14/211,501, filed on Mar. 14, 2014, now abandoned, which is a continuation-in-part of application No. 13/529,470, filed on Jun. 21, 2012, now abandoned.

(60) Provisional application No. 61/499,265, filed on Jun. 21, 2011.

(51) Int. Cl.
| | | |
|---|---|---|
| *A01N 57/12* | (2006.01) | |
| *A01N 33/12* | (2006.01) | |
| *A61K 31/14* | (2006.01) | |
| *A01N 25/02* | (2006.01) | |
| *A01N 25/30* | (2006.01) | |
| *A01N 31/02* | (2006.01) | |
| *A01N 47/44* | (2006.01) | |

(52) U.S. Cl.
CPC .............. *A01N 57/12* (2013.01); *A01N 33/12* (2013.01); *A61K 31/14* (2013.01)

(58) Field of Classification Search
CPC ........ A01N 57/12; A01N 25/02; A01N 25/30; A01N 31/02; A01N 33/12; A01N 47/44; A01N 25/22; A61K 31/14
See application file for complete search history.

(56) References Cited

U.S. PATENT DOCUMENTS

| | | |
|---|---|---|
| 2,577,773 A | 12/1951 | Lambert |
| 3,419,006 A | 12/1968 | King |
| 3,968,246 A | 7/1976 | Merianos et al. |
| 4,203,872 A | 5/1980 | Flanagan |
| 4,278,664 A | 7/1981 | Van Cleave |
| 4,321,277 A | 3/1982 | Saurino |
| 4,336,151 A | 6/1982 | Like et al. |
| 4,657,758 A | 4/1987 | Goldemberg et al. |
| 4,721,724 A | 1/1988 | Stettendorf et al. |
| 4,797,420 A | 1/1989 | Bryant |
| 5,181,914 A | 1/1993 | Zook |
| 5,284,833 A | 2/1994 | McAnalley et al. |
| 5,346,692 A | 9/1994 | Wohlrab et al. |
| 5,362,422 A | 11/1994 | Masters |
| 5,439,682 A | 8/1995 | Wivell et al. |
| 5,550,163 A | 8/1996 | Ding et al. |
| 5,661,170 A | 8/1997 | Chodosh |
| 5,908,865 A | 6/1999 | Doi et al. |
| 5,968,986 A | 10/1999 | Dyer |
| 5,994,383 A | 11/1999 | Dyer et al. |
| 6,013,677 A | 1/2000 | Dyer |
| 6,022,549 A | 2/2000 | Dyer |
| 6,022,551 A * | 2/2000 | Jampani ................. A01N 31/16 424/405 |
| 6,087,400 A | 7/2000 | Dyer et al. |
| 6,476,218 B1 | 11/2002 | Choque et al. |
| 6,479,039 B1 | 11/2002 | Dyer et al. |
| 6,503,952 B2 | 1/2003 | Modak et al. |
| 7,244,418 B2 | 7/2007 | Dyer et al. |
| 8,188,006 B2 | 5/2012 | Leeper et al. |
| 8,193,244 B1 | 6/2012 | Stockel et al. |
| 2005/0192547 A1 | 9/2005 | Modak et al. |
| 2005/0238602 A1 | 10/2005 | Modak et al. |
| 2007/0048345 A1* | 3/2007 | Huang ................... A01N 31/02 424/405 |
| 2008/0255014 A1 | 10/2008 | Luu et al. |
| 2009/0118152 A1* | 5/2009 | Lam ..................... A61K 8/0208 510/120 |

OTHER PUBLICATIONS

Dyer et al., Testing a New Alcohol-Free Hand Sanitizer to Combat Infection, Aom Journal, Aug. 1998, vol. 68, No. 2.
Uniqema Personal Care, Phospholipids—A Natural Choice for Personal Care, Business Briefing: Global Cosmetics Manufacturing 2004.
Dyer et al., Measuring Skin Antibacterial Activity Skin Drying and Dermal Tolerance, Mar. 9, 2006, The Glove Juice Human Subject Independent Study (per FDA protocol at California State University-Fresno).
Lonza, Uniquat QAC 50 Uniquat QAC 80; 2 pgs. bio.lonza.c,om/.../ Lonza_ProductDataSheets_Uniquat_QAC; revised Oct. 19, 2009. pp. 2.
Federal Register, Topical Antimicrobial Drug Products for over-the counter human use; Tentative final monograph for first aid antiseptic drug products, vol. 56, No. 140, Monday, Jul. 22, 1991.
SafeHands Points to the Dangers of Alcohol-Based Hand Sanitizers, Feb. 6, 2009, www.infectioncontrol today.
"Woodward's HandClens Antimicrobial Foam Hand Wash," Marketing Brochure, Woodward Laboratories, Inc., 2014, www.woodwardlabs.com, 2 pages.
Dyer et al., "Testing a New Alcohol-Free Hand Sanitizer to Combat Infection," AORN Journal; Aug. 1998, vol. 68, No. 2; pp. 239-251.
Senior, "Some Observations on the Formulation and Properties of Chlorhexidine," J. Soc. Cosmet. Chem.: 24. 1973; Society of Cosmetic Chemists of Great Britain; pp. 259-278.

(Continued)

*Primary Examiner* — Mark V Stevens

(74) *Attorney, Agent, or Firm* — Allen, Dyer, Doppelt & Gilchrist, P.A.

(57) ABSTRACT

An antimicrobial composition includes benzalkonium chloride in an amount of 0.06% w/w to 0.19% w/w and cocamidopropyl PG-dimonium chloride phosphate in an amount of 0.6% w/w to 1.9% w/w. The composition also includes propylene glycol in an amount of 0.4% w/w to 1.2% w/w and triethylene glycol in an amount of 0.1% w/w to 0.3% w/w. A polysorbate is included in an amount of 0.02% w/w to 0.08% w/w and water in an amount of 96.0% w/w to 99.0% w/w.

15 Claims, No Drawings

(56) References Cited

OTHER PUBLICATIONS

Freundlich et al., "Triclosan Derivatives: Towards Potent Inhibitors of Drug-Sensitive and Drug-Resistant *Mycobacterium tuberculosis*," ChemMedChem: 4; 2009; pp. 241-248.
"Triclosan: White Paper Prepared by the Alliance for Prudent Use of Antibiotics (APUA)," Jan. 2011; pp. 1-18.
Koburger et al., "Standardized Comparison of Antiseptic Efficacy of Triclosan, PVP-Iodine, Octenidine Dihydrochloride, Polyhexanide and Chlorhexidine Digluconate," J Antimicrob Chemother: 65; 2010; pp. 1712-1719.
Redfors et al., "Effects of Mannitol Alone and Mannitol Plus Furosemide on Renal Oxygen Consumption, Blood Flow and Glomerular Filtration After Cardiac Surgery," Intensive Care Med: 35; 2009; pp. 115-122.
Richards et al., "Enhancement of Benzalkonium Chloride and Chlorhexidine Acetate Activity Against Pseudomonas Aeruginosa by Aromatic Alcohols," Journal of Pharmaceutical Sciences, Dec. 1973, vol. 62. No. 12; pp. 2035-2037.
Dutta et al., "A Laboratory Assessment of Factors That Affect Bacterial Adhesion to Contact Lenses," Biology: 2; 2013; pp. 1268-1281.
K.K. Singh, "Handbook on Cosmetics: Processes, Formulae With Testing Methods," Asia Pacific Business Press, Inc.; 2010; 2 pages.
Wedderburn, "Preservation of Toilet Preparations Containing Nonionics," Journal of the Society of Cosmetic Chemists: Apr. 14, 1958; pp. 210-228.
Araujo et al.,"The Influence of Interfering Substances on the Antimicrobial Activity of Selected Quaternary Ammonium Compounds," International Journal of Food Science; Aug. 1, 2013; vol. 2013; pp. 1-9.
Kim et al., "Macrophage Depletion Ameliorates Glycerol-Induced Acute Kidney Injury in Mice," Nephron Experimental Nephrology 2014; 128:21-29; published online Nov. 5, 2014; pp. 21-29.

* cited by examiner

WATER BASED ANTIMICROBIAL COMPOSITION USING BENZALKONIUM CHLORIDE AND COCAMIDOPROPYL PG-DIMONIUM CHLORIDE PHOSPHATE

RELATED APPLICATIONS

This is a continuation-in-part application of Ser. No. 14/211,501 filed Mar. 14, 2014, which is a continuation-in-part application of Ser. No. 13/529,470 filed Jun. 21, 2012, which claimed priority to provisional application Ser. No. 61/499,265, filed Jun. 21, 2011, the disclosures which are hereby incorporated by reference in their entirety.

FIELD OF THE INVENTION

The invention relates to antimicrobial compositions, and more particularly, to antimicrobial compositions that use quaternary ammonium based active ingredients, such as benzalkonium chloride in combination with phospholipids and glycols.

BACKGROUND

The wide variety of instant hand sanitizers available to consumers may be grouped into two categories: alcohol-free and alcohol-containing. Of the former category, quaternary ammonium compounds are most frequently employed as the antimicrobial active ingredient. Of the latter category, ethanol at a concentration range of 62-70% w/w is most readily available on the market. In general, both alcohol-free and alcohol-containing products are effective at reducing germs on the skin with a single use. With repeated use, however, alcohol-free products show a significant persistence of antimicrobial activity while alcohol-containing products appear to increase the skin's ability to carry disease-causing pathogens.

An antimicrobial active ingredient that has been used to sanitize hands is chlorhexidine (CHX). In one aspect, chlorhexidine gluconate (CHX-gluconate), a particular salt of chlorhexidine and gluconate, is widely used as a surgical hand scrub and pre-operation skin scrub. The commercially available antiseptic scrub HIBICLENS®, for example, contains 4% CHX-gluconate.

The parent application Ser. No. 14/211,501 and grand-parent application Ser. No. 13/529,470 disclose the use of chlorhexidine gluconate in combination with a quaternary ammonium based active ingredient, e.g., benzalkonium chloride. CHX-gluconate is not always desirable in combination with benzalkonium chloride because of regulatory or other issues. It is desirable, however, in certain instances, to use an antimicrobial composition that does not use CHX-gluconate. It has also been found that benzalkonium chloride when used in combination with certain surfactants may damage the skin or cause irritation that is bothersome to the user. The degree of irritation may depend on the surfactant, but it is problematic in certain instances. It is also desirable to use benzalkonium chloride in combination with other ingredients that are chosen to be effective and overcome the drawbacks associated when benzalkonium chloride that is used with surfactants may damage or irritate skin. It is desirable to find a composition using benzalkonium chloride that is formulated with a surfactant and other compounds that mitigate this effect of irritating the user's skin, but maintain effectiveness as an antimicrobial without employing CHX-gluconate.

SUMMARY

According to one aspect of the invention, an antimicrobial composition includes benzalkonium chloride and a phosphate with glycols such as propylene glycol and triethylene glycol. It includes a polysorbate and a large amount of water, such as over 95% water, to form an aqueous solution that is effective as an antimicrobial and does not harm or irritate the skin. The combination of ingredients work together in an effective manner as an antimicrobial composition.

An antimicrobial composition includes benzalkonium chloride in an amount of 0.06% w/w to 0.19% w/w, and cocamidopropyl PG-dimonium chloride phosphate in an amount of 0.6% w/w to 1.9% w/w. Propylene glycol is in an amount of 0.4% w/w to 1.2% w/w and triethylene glycol in an amount of 0.1% w/w to 0.3% w/w. A polysorbate is in an amount of 0.02% w/w to 0.08% w/w, and water is in an amount of 96.0% w/w to 99.0% w/w.

The benzalkonium chloride may be in an amount of 0.09% w/w to 0.17% w/w. The cocamidopropyl PG-dimonium chloride phosphate may be in an amount of 0.8% w/w to 1.6% w/w. The propylene glycol may be in an amount of 0.6% w/w to 1.0.% w/w and the triethylene glycol may be in an amount of 0.14% w/w to 0.26% w/w. The polysorbate may be in an amount of 0.04% w/w to 0.06% w/w. The water may be in amount of 97.0% w/w to 98.0% w/w.

In an example, the polysorbate may comprise polysorbate-20. The benzalkonium chloride may be in an amount of about 0.13% w/w. The cocamidopropyl PG-dimonium chloride phosphate may be in an amount of about 1.25% w/w. The propylene glycol may be in an amount of about 0.8% w/w and the triethylene glycol may be in an amount of about 0.2% w/w. The polysorbate may be in an amount of about 0.05% w/w.

DETAILED DESCRIPTION

In the Summary above and in the Detailed Description, reference is made to particular features (including method steps) of the invention. It is to be understood that the disclosure of the invention in this specification includes all possible combinations of such particular features. For example, where a particular feature is disclosed in the context of a particular aspect or embodiment of the invention, that feature can also be used, to the extent possible, in combination with and/or in the context of other particular aspects and embodiments of the invention, and in the invention generally.

The term "comprises" is used herein to mean that other ingredients, features, steps, etc. are optionally present. When reference is made herein to a method comprising two or more defined steps, the steps can be carried in any order or simultaneously (except where the context excludes that possibility), and the method can include one or more steps which are carried out before any of the defined steps, between two of the defined steps, or after all of the defined steps (except where the context excludes that possibility).

In this section, the invention will be described more fully with reference to certain preferred embodiments. This invention may, however, be embodied in many different forms and should not be construed as limited to the embodiments set forth herein. Rather, these embodiments are provided so that this disclosure will be thorough and complete, and will convey preferred embodiments of the invention to those skilled in the art.

The composition overcomes the problems associated when benzalkonium chloride is used with surfactants and the composition may damage or irritate the skin. A specific combination and range of ingredients are used with a specific concentration and range of benzalkonium chloride and formulated to mitigate skin irritation. It has been found that an antimicrobial composition that includes benzalkonium chloride in an amount of 0.06% w/w to 0.19% w/w with specific phosphates, glycols and other components may include a large amount of water and be effective against microbials and not damage skin. In an example, the composition includes cocamidopropyl PG-dimonium chloride phosphate in an amount of 0.6% w/w to 1.9% w/w. The composition also includes propylene glycol in an amount of 0.4% w/w to 1.2% w/w. Triethylene glycol is included in an amount of 0.1% w/w to 0.3% w/w. A polysorbate is included in an amount of 0.02% w/w to 0.08% w/w. In an example, the polysorbate is formed as polysorbate-20. The composition may also include trace amounts of a fragrance at around 0.02% w/w to about 0.08% w/w and a color agent such as peach, rose, aqua or other color component that is about 0.05%.

In an example, the benzalkonium chloride is in an amount of 0.09% w/w to 0.17% w/w and in a preferred example, is about 0.13% w/w. The cocamidopropyl PG-dimonium chloride phosphate is in an amount of 0.08% w/w to 1.6% w/w in an example, and in a preferred example, is about 1.25% w/w. The propylene glycol is in an amount of 0.6% w/w to 1.0% w/w, and in a preferred example, is in an amount of 0.8% w/w. The triethylene glycol is in an amount of 0.14% w/w to 0.26% w/w, and in a preferred example, is about 0.2% w/w.

The water is in an amount of about 97.0% w/w to about 98.0% w/w. The polysorbate is in an amount in a preferred example of about 0.05% w/w and is formed as polysorbate-20. In an example, the benzalkonium chloride may be supplied as Nobac BZK USP NF 50% solution at a preferred amount of about 0.26% by mason. The cocamidopropyl PG-dimonium chloride phosphate may be supplied by Croda as Arlasilk PTC LQ-(AP). The fragrance may be supplied by Cosmo International.

The composition has been found effective. It includes the polysorbate, namely, the polysorbate-20, and the other ingredients without the chlorhexidine gluconate. It includes the benzalkonium chloride, cocamidopropyl PG-dimonium chloride phosphate, propylene glycol, triethylene glycol, and water. The composition works as an antimicrobial and anti-bacterial with an effectiveness similar to the composition as disclosed in the parent applications that include chlorhexidine gluconate.

Removing the chlorhexidine gluconate and maintaining the benzalkonium chloride, cocamidopropyl PG-dimonium chloride phosphate, propylene glycol, triethylene glycol, and large amount of water together with the polysorbate-20 has been found effective and safe. The polysorbate-20 is about 25-40% by weight of the amount of benzalkonium chloride in an example, and 30-35% in another example. A large amount such as 1.25% by weight of cocamidopropyl PG-dimonium chloride phosphate is used. The polysorbate is an emulsifier and is able to solubilize essential oils into water-based products and is derived from PEG-ylated sorbitan as a derivative of sorbitol and esterified with fatty acids. Polysorbate-20 is also referred to as polyoxyethylene (20) sorbitan monolaurate with the numeral twenty referring to the total number of oxyethylene-$(CH_2CH_2O)$-groups in the molecule. This number twenty following that polysorbate is related to the type of fatty acid associated with the polyoxyethylene sorbitan part of the molecule. The monolaurate is indicated by the number twenty. The polysorbate-20 is a polysorbate surfactant that is stable and has relative non-toxicity. It is operable as a wetting agent and is helpful to prevent non-specific antibody binding that is useful in the antimicrobial composition. It operates with the phosphate of cocamidopropyl PG-dimonium chloride phosphate and is dissolved and operable with the buffer as a wash to remove unbound immunologicals. It may saturate binding sites on surfaces to stabilize a proteins purified protein derivative (PPD) solution and operate as a solubilizing agent of membrane proteins and helpful in antimicrobial compositions.

Benzalkonium chloride operates as a cationic surfactant as a quaternary ammonium compound and organic salt and operates as the biocide and phase transfer agent. It is a surfactant and dissolves the lipid phase and increases drug penetration as an excipient. As noted before, it has efficacy for intermolecular interactions and dissociates cellular membrane lipid bilayers in bacteria and microbials for micellular permeability controls in induced leakage of cellular contents. The enzymes that control many respiratory and metabolic cellular activities are deactivated. It is known that appropriate excipients can greatly enhance the spectrum, performance and detergency and the composition as noted above and meets such difficult standards with minimized deactivation of benzalkonium solutions with organic and inorganic contamination and use as an antimicrobial.

In an example, the benzalkonium chloride can be provided at USPNF 50% and in a preferred example would be about 2.6% w/w. The benzalkonium chloride and polysorbate-20 operate in conjunction with the cocamidopropyl PG-dimonium chloride phosphate that also operates as a surfactant and to a degree a foam booster. It may operate as a preservative with a moisturizing effect. It is a quaternary ammonium salt with its RCO-group representing a coconut acid moiety. It may operate as a counter-irritant from anionic surfactants and is not adversely effected by solution pH, anionic or non-ionic surfactants or preservatives, thus, making it operable not only with the benzalkonium chloride and polysorbate-20, but also with the propylene glycol and triethylene glycol and soluble with the water. It may appear that the use of the propylene glycol and triethylene glycol are mutually exclusive of each other and with the other components, but in operation, the components as described is effective. The propylene glycol is about four times greater in w/w concentration than the triethylene glycol and can range from 3:1 to 5:1. It may operate not only as an antimicrobial, but as a solvent to help solvate certain compounds and associated microbials. One aspect is it exerts high levels of biochemical oxygen demand (BOD) during degradation in surface waters and consumes oxygen as an added benefit when microbial populations decompose the propylene glycol. The triethylene glycol is hygroscopic and dehumidifies fluids. These components interoperate with each other to provide an effective antimicrobial.

There now follows a description of the composition as described in the parent and grandparent applications using the chlorhexidine gluconate, benzalkonium chloride and other components such as the cocamidopropyl PG-dimonium chloride phosphate.

Since CHX-gluconate and BAC, individually, show excellent antimicrobial effectiveness, one of the goals of the research described here was to prepare antimicrobial compositions that use a combination of CHX-gluconate and BAC as the antimicrobial active ingredients, but doing so was difficult. Because CHX-gluconate is a zwitterion, it tended to precipitate when mixed with BAC, which reduced the antimicrobial effectiveness of CHX-gluconate, thereby defeating the purpose of combining the two ingredients. It was found that, in an aqueous solution containing BAC, CHX-gluconate is stably maintained (i.e. without precipitating over time) by including a phospholipid. Although not intended to be limiting, a particular phospholipid useful for this purpose was found to be cocamidopropyl PG-dimonium chloride phosphate. The structure of the sodium salt of cocamidopropyl PG-dimonium chloride phosphate is shown below.

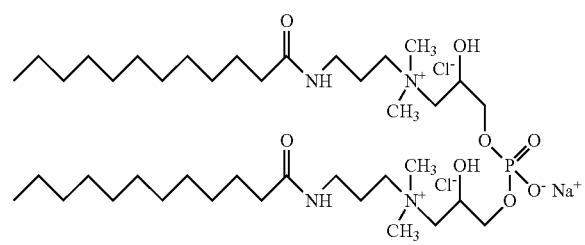

Sodium Cocamidopropyl
PG-Dimonium Chloride Phosphate

Cocamidopropyl PG-dimonium chloride phosphate is a phospholipid composed predominantly of diester phosphatides with multiple long alkyl chain groups. It is derived from coconut oil and is said to be compatible with the natural lipids found in the skin's epidermal layers. Advantageously, cocamidopropyl PG-dimonium chloride phosphate behaves as a broad spectrum antimicrobial against mold, gram-positive, and gram-negative bacteria. A published 2004 report by Uniqema Personal Care in *Business Briefing: Global Cosmetics Manufacturing* at pages 1-4, which is hereby incorporated by reference in its entirety, describes additional details about cocamidopropyl PG-dimonium chloride phosphate. As of the date this application was filed, this reference was available online at: http://www.touchbriefings.com/pdf/846/Uniqema.pdf. A preferred cocamidopropyl PG-dimonium chloride phosphate is commercially available from Croda under the name ARALISK PTC.

Remarkably, it was unexpectedly discovered that the when CHX-gluconate, BAC, and a phospholipid, were mixed to make the antimicrobial composition, the combination provided a synergistic antimicrobial enhancement. More particularly, the mixture showed a 100 fold enhanced measurement of antimicrobial effectiveness relative to the combined measurements of antimicrobial effectiveness of chlorhexidine gluconate, benzalkonium chloride, and cocamidopropyl PG-dimonium chloride phosphate when measured individually. This synergistic enhancement of antimicrobial effectiveness allows for low concentrations of chlorhexidine gluconate, benzalkonium chloride, and cocamidopropyl PG-dimonium chloride phosphate to be used in the compositions of the invention without diminishing the antimicrobial effectiveness.

Preferred concentrations of the various ingredients will now be discussed with respect to % w/w, which refers to the percent, by weight, of each ingredient relative to the total weight of the composition.

Certain preferred embodiments of the antimicrobial compositions are now described. In general, an antimicrobial composition of the invention includes the active ingredients and one or more optional ingredients dispersed in an aqueous mixture. Preferably the composition includes at least about 60% w/w water, more preferably about 60% w/w to about 99% w/w water, and even more preferably about 65% w/w to about 98% w/w water.

In a preferred embodiment, the antimicrobial composition includes a stable and antimicrobially effective aqueous blend of at least one chlorhexidine compound, at least one quaternary ammonium compound, and at least one phospholipid compound. The term "stable" means that the at least one chlorhexidine compound does not precipitate when exposed to the at least one quaternary ammonium compound. The phrase "antimicrobially effective" describes a composition that inhibits the growth of and/or kills microbes such as bacteria.

Through experimentation, it was discovered that a stable and antimicrobially effective aqueous blend of these components is achieved when the concentration of the least one chlorhexidine compound is about 0.001% to about 0.2% w/w, the concentration of the least one quaternary ammonium compound is about 0.001% to about 0.3% w/w, and the concentration of the least one phospholipid compound is about 0.5% to about 1.5% w/w.

Preferred examples of chlorhexidine compounds that may be used in accordance with the invention include, but are not limited to: chlorhexidine free base, chlorhexidine diphosphanilate, chlorhexidine digluconate, chlorhexidine diacetate, chlorhexidine dihydrochloride, chlorhexidine dichloride, chlorhexidine dihydroiodide, chlorhexidine diperchlorate, chlorhexidine dinitrate, chlorhexidine sulfate, chlorhexidine sulfite, chlorhexidine thiosulfate, chlorhexidine di-acid phosphate, chlorhexidine difluorophosphate, chlorhexidine diformate, chlorhexidine dipropionate, chlorhexidine diiodobutyrate, chlorhexidine di-n-valerate, chlorhexidine dicaproate, chlorhexidine malonate, chlorhexidine succinate, chlorhexidine malate, chlorhexidine tartrate, chlorhexidine dimonoglycolate, chlorhexidine monodiglycolate, chlorhexidine dilactate, chlorhexidine chlorhexidine di-isothionate, chlorhexidine dibenzoate, chlorhexidine dicinnamate, chlorhexidine dimandelate, chlorhexidine di-isophthalate, chlorhexidine di-2hydroxynaphthoate, and chlorhexidine embonate. As discussed above, a particularly preferred example is chlorhexidine gluconate.

Preferred examples of quaternary ammonium compounds that may be used in accordance with the invention include, but are not limited to: benzalkonium chloride (BAC), benzethonium chloride, other benzalkonium or benzethonium halides, cetylpyridinium chloride, dequalinium chloride, N-myristyl-N methylmorpholinium methyl sulfate, poly[N-[3-(dimethylammonio)propyl]-N'-[3-(ethyleneoxyethelene dimethylammonio)propyl]urea dichloride], alpha-4-[1-tris (2-hydroxyethyl)ammonium chloride-2-butenyl]-omegatris (2-hydroxyethyl)ammonium chloride, alpha4-[1-tris(2hydroxyethyl)ammonium chloride-2-butenyl]poly[1-dimethyl ammonium chloride-2-butenyl]-omega-tris(2hydroxyethyl) ammonium chloride, poly[oxyethylene(dimethyliminio)ethylene(dimethyliminio)-ethylene dichloride], ethyl hexadecyl dimethyl ammonium ethyl sulfate, dimethyl ammonium ethyl sulfate, dimethylethyl-benzyl ammonium chloride, dimethylbenzyl ammonium chloride, cetyldimethylethyl ammonium bromide, monoalkyltrimethyl ammonium salts, dialkyldimethyl ammonium salts, heteroaromatic ammonium salts, polysubstituted quaternary ammonium salts, bis-quaternary ammonium salts, and polymeric quaternary ammonium salts, n-alkyl dialkyl benzyl ammonium chlorides, n-alkyl ($C_{12}$, $C_{14}$, $C_{16}$) dimethyl benzyl ammonium chloride and organosilicon-substituted quaternary ammonium compounds such as 3-(trimethoxysilyl propyloctadecyldimethyl ammonium chloride.

Preferred examples of phospholipids that may be used in accordance with the invention include, but are not limited to: PG-dimonium chloride phosphates such as cocamidopropyl PG-dimonium chloride phosphate.

In such embodiments, the at least one chlorhexidine compound is preferably chlorhexidine gluconate, the at least one quaternary ammonium compound is benzalkonium chloride, and the at least one phospholipid compound is cocamidopropyl PG-dimonium chloride phosphate.

In another preferred embodiment, the antimicrobial composition includes an aqueous solution of about 0.001% to about 0.2% w/w chlorhexidine gluconate, about 0.001% to about 0.3% w/w benzalkonium chloride, and about 0.5% to about 1.5% w/w cocamidopropyl PG-dimonium chloride phosphate. It may also include about 0.05% to about 0.5% w/w triethylene glycol and about 0.05% to about 0.8% w/w propylene glycol. In an even more particular example of this embodiment, the concentration of chlorhexidine gluconate is about 0.2% w/w, the concentration of benzalkonium chloride is about 0.13% w/w, and the concentration of cocamidopropyl PG-dimonium chloride phosphate is about 1.25% w/w.

In another preferred embodiment, the antimicrobial composition includes an enhanced synergistically effective antimicrobial mixture of chlorhexidine gluconate, benzalkonium chloride, and cocamidopropyl PG-dimonium chloride phosphate. Here, the enhanced synergistically effective antimicrobial mixture shows an enhanced measurement of antimicrobial effectiveness relative to the combined measurements of antimicrobial effectiveness of chlorhexidine gluconate, benzalkonium chloride, and cocamidopropyl PG-dimonium chloride phosphate when measured individually. Antimicrobial effectiveness may be measured using conventional protocols such as minimum inhibitory concentration testing, bacterial counting, kill time studies, or the like.

In this embodiment, the preferred concentration of chlorhexidine gluconate is about 0.001% to about 0.2% w/w, the preferred concentration of benzalkonium chloride is about 0.001% to about 0.3% w/w, and the preferred concentration of cocamidopropyl PG-dimonium chloride phosphate about 0.5% to about 1.5% w/w. In a more particular example, the concentration of chlorhexidine gluconate is about 0.15% w/w, the concentration of benzalkonium chloride is about 0.13% w/w, and the concentration of cocamidopropyl PG-dimonium chloride phosphate is about 1.25% w/w. The composition may also include about 0.05% w/w to about 0.5% w/w triethylene glycol and 0.05% w/w to about 0.8% w/w propylene glycol.

The pH of the antimicrobial composition is preferably maintained between about 3 and about 9, more preferably between about 5 and about 8. Quaternary ammonium compounds are typically unstable below pH 3 or above pH 9, and are usually incompatible with anionic soaps and with moderate concentrations of anionic detergents. In particular, anionic soaps and surfactants have been found to neutralize quaternary ammonium compounds.

Optionally one or more preservatives may be added to the antimicrobial composition, in order to preserve the antimicrobial active ingredients. The most commonly used preservatives in conventional pharmaceutical formulations are the parabens (including, but not limited to methyl, ethyl, propyl, pentyl, hexyl and heptyl paraben), and phenoxyethanol. Preferably excluded from the embodiments of the invention are preservatives which act as formaldehyde donors, including diazolidinyl urea, imidazolidinyl urea, among others.

Another optional ingredient that can be included in the antimicrobial composition is a thickener. The thickener may be used for the stabilization of the final composition, and for the regulation of viscosity, which may vary widely according to the desired application. Examples of thickeners include, but are not limited to methylcellulose, hydroxypropylmethylcellulose, hydroxypropylcellulose, carboxymethylcellulose and methyl cellulose, and lysophosphatidic acid.

Another optional ingredient that can be included in the compositions is a polyol co-solvent. This can be conveniently added for the dissolution or stabilization of certain ingredients. The polyol co-solvent is preferably selected from the glycol class of compounds. Preferred glycols include propylene glycol, polyethylene glycol, and triethylene glycol. Such polyethylene glycols include the polyalkene glycol products with chemical structures having 2-3 carbons in the alkene moiety, and a mean molecular weight ranging from 200-4000. These compounds, if used, are present in amounts generally ranging from about 0.01% w/w to about 15.0% w/w, based on the total weight of the composition, or more preferably from about 0.05% w/w weight percent to about 1.0% w/w percent.

If desired, one or more pH adjusting compounds may be included. Such pH adjusting compounds may be organic or inorganic acids and bases alone or in combination with their respective salts. Commonly used pH lowering agents are citric acid, sorbic acid, ascorbic acid, malic acid, and succinic acid among many others. Commonly used pH raising agents include triethanolamine, ammonium hydroxide, potassium hydroxide, sodium hydroxide, and other hydroxides. The amount of the pH adjusting compound used is the amount needed to adjust the pH to the desired value.

The antimicrobial compositions of the invention are preferably used as instant hand sanitizers. Accordingly, they may be packaged in dispensing bottles and dispensed onto the hands of a user. They are preferably present in a form that is antimicrobial when applied topically to skin. Suitable forms for topical application include, but are not limited to creams, gels, suspensions, or the like. The antimicrobial compositions are particularly useful to sanitize hands in situations where conventional soap and water hand washing facilities are not available or are impractical to use.

In a preferred method of use aspect of the invention, the antimicrobial composition is used to sanitize the skin of a subject in need thereof by applying an effective amount of the antimicrobial composition to the subject. Here, an "effective amount" is an amount that is sufficient to affect a microbe, such as by inhibiting microbial growth or killing the microbe. In practice, the subject may dispense the antimicrobial composition onto the subject's hands and rub the hands together.

Other exemplary uses for the antimicrobial compositions include, but are not limited to: formulations for oral use such as a mouthwash or dentifrice; formulations for topical use such as a skin sanitizer, surgical scrub and preparation, and handwash; treatment of infections of the skin or mouth area in a human; veterinary medicament for animal skin, hooves, claws, fur, or teeth; nail paints and polishes; indwelling medical devices; venous access catheters; gastric and enteric long term feeding tubes; neurological shunting tubing; polytetrafluoroethane graft materials (both for tissue patch and vascular conduits); endotracheal and tracheostomy tubing; intravenous interarterial tubing; indwelling urinary catheters; joint implants; soft tissue implants, orthopaedic external fixation devices, (including hardware necessary to secure them to the bone); medication ampules; intravenous polyethylene fluid storage/delivery bag systems (including those for blood and blood products); mouth rinses (including swish and swallow preparations); skin preparations; bowel preparations; footwear inserts; and towelettes.

The antimicrobial composition may also be used in formulations not intended for application or administration directly to a subject, such as, for example, as a surface, air, or water sanitizer.

EXAMPLES

The following examples are provided for the purpose of illustration and do not limit the scope of the invention in any way.

Example 1

Preparation of an Exemplary Antimicrobial Composition

This example shows how an antimicrobial composition was prepared in accordance with the invention.

The antimicrobial composition prepared in this example contained: 0.15% w/w chlorhexidine gluconate; 0.13% w/w benzalkonium chloride; 1.25% w/w cocamidopropyl PG-dimonium chloride; 0.2% w/w triethylene glycol; 0.8% propylene glycol; and 96.6% deionized water.

The composition was prepared by using commercially available materials. UNIQUAT QAC 80 (Lonza) was the source of the BAC. ARLASILK PTC was the source of the cocamidopropyl PG-dimonium chloride.

Example 2

Stability Testing

This example shows how the stability testing was performed and how stable compositions were identified.

In these experiments, numerous combinations of CHX-gluconate and BAC were tested to determine the combinations and concentrations that yielded stable antimicrobial compositions. It was discovered that cocamidopropyl PG-dimonium chloride phosphate was effective as a CHX-gluconate stabilizer. As described previously, a stable composition is one for which CHX-gluconate did not precipitate over time.

The samples were subjected to three consecutive freeze/thaw cycles over a five day period. The freezing temperature was −14 Celsius and the thawing temperature was 37 Celsius. Stability was assessed by visually inspecting each sample for the formation of a precipitate and/or discoloration.

The concentration ranges for the various ingredients for the stable samples were: about 0.001% to about 0.15% w/w chlorhexidine gluconate; about 0.001% to about 0.3% w/w benzalkonium chloride; about 0.5% to about 1.5% w/w cocamidopropyl PG-dimonium chloride phosphate; about 0.05% w/w to about 0.5% w/w triethylene glycol; and about 0.05% w/w to about 0.8% w/w propylene glycol.

Example 3

Antimicrobial Effectiveness Testing

This example shows how the antimicrobial effectiveness of certain antimicrobial compositions prepared in accordance with the invention was tested and describes the unexpected result that CHX-Gluconate, BAC, and cocamidopropyl PG-dimonium chloride phosphate synergistically enhance the antimicrobial effectives when compared to the antimicrobial effectiveness of each of these tested individually.

The tests were performed on broth cultures that were passed through at least three consecutive daily transfers but no more than ten daily transfers. The broth cultures were diluted with the appropriate broth to obtain an inoculum count of $6 \times 10^8$ to $1 \times 10^9$ CFU/ml (Mac Farland Standard ~2.0 to 3.0). The test article was used undiluted. The exposure time and temperature was 15 seconds at 25±1° C., respectively. All tests involving the test article were conducted in triplicate. A 4.95 gram sample of the test article was placed in a sterile, screw-top 50 ml polyethylene tube at 25±1° C. The test article was inoculated with 0.05 ml of the test organism at the appropriate concentration. The tube contents were neutralized by the addition of 45 ml of Neutralizer (Tryptic or Trypticase Soy Broth (TSB) with 10% TWEEN 80, 3% Lecithin, 0.5% Sodium thiosulfate and 0.1% Histidine, pH 7.2±0.1) followed by vortexing. One ml of the neutralized sample ($10^{-1}$ dilution) was serially diluted in 10-fold steps to $10^{-6}$ for the test article and to $10^{-7}$ for the numbers control using tubes containing 9 ml of AOAC Neutralizer blanks. An inoculum count was determined by 10-fold serial dilutions to $10^{-8}$ using tubes containing 9 ml of AOAC phosphate buffered dilution water. The dilutions were plated in duplicate on Letheen Agar, and plates were incubated in an inverted position for the appropriate time and at a temperature appropriate for the test organism. The test organism was a single species of *Staphylococcus aureus*.

Antimicrobial effectiveness was determined by calculating the log reduction of bacteria in the test sample. For comparison, the log reduction for a 0.02% CHX-gluconate solution is 0.5, the log reduction for a 0.13% BAC solution is 0.5, and the log reduction for a 1% cocamidopropyl PG-dimonium chloride phosphate solution is 2. When added together, the total log reduction for the three ingredients tested individually is 3.

Our results showed that an antimicrobial composition composed of 0.02% CHX-gluconate, 0.13% BAC, 1% cocamidopropyl PG-dimonium chloride phosphate, 0.2% triethylene glycol, and 0.2% propylene glycol provided a log reduction of 5, which is a 100 fold increase in the antimicrobial effectiveness. This indicates that the antimicrobial compositions of the invention include an enhanced synergistically effective antimicrobial mixture of chlorhexidine gluconate, benzalkonium chloride, and cocamidopropyl PG-dimonium chloride phosphate.

The invention has been described above with reference to preferred embodiments. Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described. However, the skilled should understand that the methods and materials used and described are examples and may not be the only ones suitable for use in the invention.

Accordingly, this invention may be embodied in many different forms and should not be construed as limited to the embodiments set forth herein. Rather, these embodiments are provided so that this disclosure will be thorough, complete, and will fully convey the scope of the invention to those skilled in the art. Therefore, in the specification set forth above there have been disclosed typical preferred embodiments of the invention, and although specific terms That which is claimed is:

1. An antimicrobial composition, comprising:
benzalkonium chloride in an amount of 0.06% w/w to 0.19% w/w;
cocamidopropyl PG-dimonium chloride phosphate in an amount of 0.6% w/w to 1.9% w/w;
propylene glycol in an amount of 0.4% w/w to 1.2% w/w;
triethylene glycol in an amount of 0.1% w/w to 0.3% w/w;
a polysorbate in an amount of 0.02% w/w to 0.08% w/w; and
water in an amount of at least 96.0% w/w.

2. The antimicrobial composition according to claim 1, wherein the benzalkonium chloride is in an amount of 0.09% w/w to 0.17% w/w.

3. The antimicrobial composition according to claim 1, wherein the cocamidopropyl PG-dimonium chloride phosphate is in an amount of 0.8% w/w to 1.6% w/w.

4. The antimicrobial composition according to claim 1, wherein the propylene glycol is in an amount of 0.6% w/w to 1.0% w/w and the triethylene glycol is in an amount of 0.14% w/w to 0.26% w/w.

5. The antimicrobial composition according to claim 1, wherein the polysorbate is in an amount of 0.04% w/w to 0.06% w/w.

6. The antimicrobial composition according to claim 1, wherein the polysorbate comprises polysorbate-20.

7. The antimicrobial composition according to claim 1, wherein the benzalkonium chloride is in an amount of about 0.13% w/w.

8. The antimicrobial composition according to claim 1, wherein the cocamidopropyl PG-dimonium chloride phosphate is in an amount of about 1.25% w/w.

9. The antimicrobial composition according to claim 1, wherein the propylene glycol is in an amount of about 0.8% w/w and the triethylene glycol is in an amount of about 0.2% w/w.

10. The antimicrobial composition according to claim 1, wherein the polysorbate is in an amount of about 0.05% w/w.

11. An antimicrobial composition, comprising:
benzalkonium chloride in an amount of 0.09% w/w to 0.17% w/w;
cocamidopropyl PG-dimonium chloride phosphate in an amount of 0.8% w/w to 1.6% w/w;
propylene glycol in an amount of 0.6% w/w to 1.0% w/w;
triethylene glycol in an amount of 0.14% w/w to 0.26% w/w;
a polysorbate-20 in an amount of 0.04% w/w to 0.06% w/w; and
water in an amount of at least 97.0% w/w.

12. The antimicrobial composition according to claim 11, wherein the benzalkonium chloride is in an amount of about 0.13% w/w.

13. The antimicrobial composition according to claim 11, wherein the cocamidopropyl PG-dimonium chloride phosphate is in an amount of about 1.25% w/w.

14. The antimicrobial composition according to claim 11, wherein the propylene glycol is in an amount of about 0.8% w/w and the triethylene glycol is in an amount of about 0.2% w/w.

15. The antimicrobial composition according to claim 11, wherein the polysorbate-20 is in an amount of about 0.05% w/w.

* * * * *